(12) United States Patent
Deppe

(10) Patent No.: US 7,479,268 B2
(45) Date of Patent: Jan. 20, 2009

(54) STAINING AGENT IN TABLET FORM FOR MAKING VISIBLE THE FORMATION OF DENTAL PLAQUE AND METHOD FOR PRODUCING SUCH A STAINING AGENT

(75) Inventor: Marc Deppe, Issum (DE)

(73) Assignee: Hager & Werken GmbH & Co. KG, Duisburg (DE)

( * ) Notice: Subject to any disclaimer, the term of this patent is extended or adjusted under 35 U.S.C. 154(b) by 551 days.

(21) Appl. No.: 10/508,250

(22) PCT Filed: Dec. 18, 2003

(86) PCT No.: PCT/DE03/04187

§ 371 (c)(1),
(2), (4) Date: Sep. 20, 2004

(87) PCT Pub. No.: WO2004/054528

PCT Pub. Date: Jul. 1, 2004

(65) Prior Publication Data

US 2005/0214214 A1    Sep. 29, 2005

(30) Foreign Application Priority Data

Dec. 18, 2002  (DE) ............................... 102 59 640

(51) Int. Cl.
  *A61B 10/00*  (2006.01)
(52) U.S. Cl. ....................................... 424/49; 424/9.71
(58) Field of Classification Search ................ 424/9.71, 424/49
See application file for complete search history.

(56) References Cited

U.S. PATENT DOCUMENTS

| 3,723,613 A | * | 3/1973 | Block et al. ................. 424/9.71 |
| 3,903,252 A | * | 9/1975 | Stearns et al. ............... 424/9.71 |
| 4,347,233 A | * | 8/1982 | Yamauchi et al. ............ 424/9.7 |
| 5,449,521 A | * | 9/1995 | Lovrecich ................... 424/489 |

OTHER PUBLICATIONS

Chemical Abstract 140:428717, "Plaque-dyeing compositions containing pigments and specified plant extracts" (2004).*
Chemical Abstract 124:325045, "Compositions containing tar xanthene dyes and other substances for revealing dental plaque" (1996).*
Chemical Abstracts Registry Number Information for Phloxin B (1984).*

* cited by examiner

*Primary Examiner*—Frederick Krass
*Assistant Examiner*—Chris E Simmons
(74) *Attorney, Agent, or Firm*—Gudrun E. Huckett

(57) ABSTRACT

A staining agent in tablet form for making visible dental plaque contains 85 to 95% by weight lactose; 1.5 to 2.6% by weight phloxin B; 2.5 to 3.5% by weight FDA Blue No. 1; 0.15 to 0.25% by weight magnesium stearate. The staining agent is produced by direct compression tableting and can also contain 0.3 to 0.75% by weight peppermint or eucalyptus flavoring agents.

2 Claims, No Drawings

STAINING AGENT IN TABLET FORM FOR MAKING VISIBLE THE FORMATION OF DENTAL PLAQUE AND METHOD FOR PRODUCING SUCH A STAINING AGENT

BACKGROUND OF THE INVENTION

Staining agents for making visible dental plaque are known in the form of solutions, tablets, toothpaste, and gels.

U.S. Pat. No. 3,723,613 A discloses a staining agent in tablet form that contains FDC Blue No. 1 and FDC Red No. 3 in order to indicate older dental plaque in dark blue and newer dental plaque in violet-red; this provides important information in regard to the advancement of dental plaque formation and in regard to the treatment thereof.

European patent 0 421 838 B1 discloses agents for indicating dental plaque formation; the agents contain conventional water-soluble dye FDC Red No. 3. A disadvantage is that FDC Red No. 3 has an unpleasant taste; moreover, in the United States its use as a component of cosmetic products has been prohibited in the year 1989 because its innocuousness has been called into question. According to European patent 0 421 838 B1, the less bitter tasting dye FDC Red No. 40 has been proposed as a substitute dye; this dye has a stronger color intensity in comparison to other dental plaque-indicating agents, for example, FDC Blue No. 1, FDC Blue No. 2, so that these dyes are less useful as dental plaque-indicating agents than FDC Red No. 40.

In Japanese application 10175835 A, a staining agent for making visible dental plaque formation in the form of a toothpaste is described that contains phloxin as a dye.

U.S. Pat. No. 4,347,233 A discloses phloxin B in solution for caries detection.

U.S. Pat. No. 3,903,252 A discloses an agent in gel form for making visible dental plaque that contains a pharmacologically harmless organic dye component that is selected from the class of FDC Red No. 3, FDC Blue No. 1, FDC Violet No. 1 and others.

U.S. Pat. No. 4,459,227A discloses a tooth paste containing FBC Blue No. 1 in order to make visible dental plaque. Japanese patent document 08059513 A concerns a solution that contains, inter alia, Red No. 3 and other Reds for making visible dental plaque. The same holds true for Japanese patent document 08143477 A. U.S. Pat. No. 4,431,628 A concerns a composition that contains the natural dye of sugar beets for making visible dental plaque.

SUMMARY OF THE INVENTION

The invention has the object of providing a staining agent that is available in tablet form and is therefore especially suitable for medical surveys and medical screening, for example, in schools, that with regard to health considerations is harmless, and that is able to indicate older dental plaque as well as newer dental plaque.

As a solution to this object, a staining agent in tablet form for making visible dental plaque is proposed that contains lactose in a range of approximately 85 to 95% by weight, phloxin B in the range of approximately 1.5 to 2.6% by weight, FDA Blue No. 1 in the range of approximately 2.5 to 3.5% by weight as well as magnesium stearate in the range of 0.15 to 0.25% by weight.

By using phloxin B in addition to FDA Blue No. 1, it is achieved that older dental plaque is shown in dark blue and newer dental plaque is shown in violet-red.

Aside from the medical indication for a dentist, the staining agent according to the invention that is in tablet form can be used independent of a dental examination also by individuals as an indicator for dental plaque formation so that it practically provides also a cosmetic function.

PREFERRED EMBODIMENTS OF THE INVENTION

Preferred concentrations of the individual components are as follows. Peppermint or eucalyptus flavoring agents in the range of approximately 0.3 to 0.75% by weight, preferably in the range of 0.5% by weight, can be added. A preferred composition comprises lactose in the range of approximately 92 to 95% by weight, phloxin B in the range of approximately 2 to 2.2% by weight, FDA Blue No. 1 in the range of approximately 2.7 to 3.1% by weight, as well as magnesium stearate in the range of 0.18 to 0.22% by weight. A more preferred composition contains lactose in the ranpe of approximately 94.3% by weight, phloxin B in the range of approximately 2.1% by weight. FDA Blue No. 1 in the range of 2.9% by weight, as well as magnesium stearate in the range of approximately 0.2% by weight. The employed phloxin B has the empirical formula $C_{20}H_2Br_4Cl_4Na_2O_5$ with the following structure:

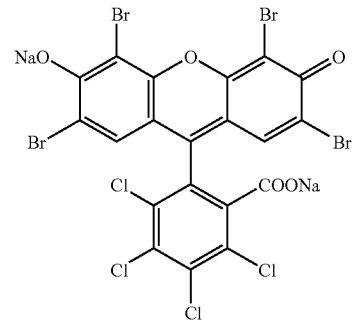

The employed FDA Blue No. 1 has the empirical formula $C_{37}H_{34}N_2Na_2O_9S_3$ with the following structure:

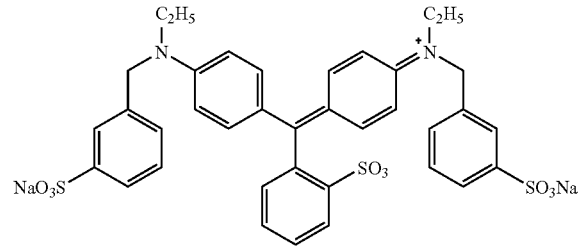

For producing the tablets, the method of direct compression tableting is selected. In this connection, micronized dye particles of dyes phloxin B and FDA Blue No. 1 are mixed with tableting agents, wherein care must be taken that the structure of the lactose is not destroyed. The tablets after tableting are exposed to a water vapor-saturated atmosphere, preferably for a duration of 2 to 3 minutes, and the tablets take on a color mottling. This color mottling occurs otherwise in the case of white tablets during storage in a somewhat humid atmosphere; however, this causes test persons to believe that the tablets are already old and are no longer useful.

The staining agent contains also peppermint or eucalyptus flavoring agents, for example, in the range of approximately 0.3 to 0.75% by weight.

What is claimed is:

1. A method for producing a staining agent for staining dental plaque, the method comprising the steps of:
   a) mixing micronized dye particles of phloxin B and Blue No. 1 with lactose and magnesium stearate as tableting agents and, optionally, peppermint or eucalyptus flavoring agents to form a mixture, wherein 85 to 95% by weight lactose, 1.5 to 2.6% by weight phloxin B, 2.5 to 3.5% by weight Blue No. 1, and 0.15 to 0.25% by weight magnesium stearate are mixed together;
   b) tableting the mixture of step a) by direct compression tableting to tablets;
   c) exposing the tablets of step b) to a water vapor-saturated atmosphere for approximately 2 to 3 minutes.

2. The method according to claim 1, wherein in step a) 0.3 to 0.75% by weight peppermint or eucalyptus flavoring agents are admixed.

* * * * *